United States Patent
Popovic et al.

(10) Patent No.: US 10,130,433 B2
(45) Date of Patent: Nov. 20, 2018

(54) REMOTE CENTER OF MOTION DEFINITION USING LIGHT SOURCES FOR ROBOT SYSTEMS

(71) Applicant: KONINKLIJKE PHILIPS N.V., Eindhoven (NL)

(72) Inventors: Aleksandra Popovic, Boston, MA (US); Haytham Elhawary, New York, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 142 days.

(21) Appl. No.: 15/115,783

(22) PCT Filed: Jan. 22, 2015

(86) PCT No.: PCT/IB2015/050483
§ 371 (c)(1),
(2) Date: Aug. 1, 2016

(87) PCT Pub. No.: WO2015/118422
PCT Pub. Date: Aug. 13, 2015

(65) Prior Publication Data
US 2017/0007335 A1    Jan. 12, 2017

Related U.S. Application Data

(60) Provisional application No. 61/935,657, filed on Feb. 4, 2014.

(51) Int. Cl.
*A61B 34/30* (2016.01)
*A61B 90/13* (2016.01)
(Continued)

(52) U.S. Cl.
CPC .............. *A61B 34/30* (2016.02); *A61B 90/11* (2016.02); *A61B 90/13* (2016.02); *B25J 9/06* (2013.01);
(Continued)

(58) Field of Classification Search
CPC ... A61B 34/30; A61B 90/11; A61B 2034/301; A61B 90/13; A61B 2090/3945;
(Continued)

(56) References Cited

U.S. PATENT DOCUMENTS

| 4,494,874 A | * | 1/1985 | DiMatteo | ............... G01B 11/24 |
| | | | | 250/205 |
| 4,836,671 A | * | 6/1989 | Bautista | ................... A61B 6/08 |
| | | | | 250/491.1 |

(Continued)

FOREIGN PATENT DOCUMENTS

| KR | 1020090123151 A | 12/2009 |
| KR | 2011030038 A | 3/2011 |
| KR | 101307951 B1 | 9/2013 |

*Primary Examiner* — R. A. Smith
*Assistant Examiner* — Tania Courson

(57) ABSTRACT

A robot system includes a robot linkage (202) having one or more arms connected by two joints (220, 222). The joints each including a joint axis of rotation (206 or 208) and a light source (128) aligned with the respective joint axis. The light sources are configured to direct light along the respective joint axis such that light from the light sources intersects at a position along an instrument (204) being held in an operational position by the robot linkage to define a remote center of motion (RCM) for the robot linkage.

21 Claims, 4 Drawing Sheets

(51) Int. Cl.
*A61B 90/11* (2016.01)
*B25J 9/06* (2006.01)
*B25J 9/12* (2006.01)
*B25J 19/00* (2006.01)
*G01B 11/27* (2006.01)
*A61B 90/00* (2016.01)

(52) U.S. Cl.
CPC ............... *B25J 9/12* (2013.01); *B25J 19/00* (2013.01); *G01B 11/27* (2013.01); *A61B 2034/301* (2016.02); *A61B 2090/3945* (2016.02); *Y10S 901/23* (2013.01); *Y10S 901/50* (2013.01)

(58) Field of Classification Search
CPC ..... B25J 19/00; B25J 9/06; B25J 9/12; G01B 11/27; Y10S 901/50; Y10S 901/23
USPC ... 33/1 PT, 1 N, 1 CC, 1 DD, 228, 276–280, 33/286, 512, 578–579, DIG. 21; 606/130
See application file for complete search history.

(56) References Cited

U.S. PATENT DOCUMENTS

| | | | | |
|---|---|---|---|---|
| 5,142,299 A | * | 8/1992 | Braun | G02B 7/32 396/107 |
| 5,212,720 A | * | 5/1993 | Landi | A61B 6/08 33/262 |
| 5,243,398 A | * | 9/1993 | Nielsen | G01C 15/002 33/290 |
| 5,298,977 A | * | 3/1994 | Shintani | H05K 13/08 356/3.03 |
| 5,397,323 A | | 3/1995 | Taylor | |
| 5,539,990 A | * | 7/1996 | Le | G01C 15/004 33/281 |
| 5,598,269 A | * | 1/1997 | Kitaevich | A61B 6/08 356/399 |
| 5,630,431 A | | 5/1997 | Taylor | |
| 5,715,052 A | * | 2/1998 | Fujino | G01N 21/94 250/559.41 |
| 5,766,126 A | | 6/1998 | Anderson | |
| 5,864,956 A | * | 2/1999 | Dong | G01B 11/26 33/227 |
| 5,877,035 A | * | 3/1999 | Fujino | G01N 21/94 257/E21.525 |
| 5,976,156 A | * | 11/1999 | Taylor | A61B 34/20 606/130 |
| 6,468,265 B1 | * | 10/2002 | Evans | A61B 34/32 600/103 |
| 6,693,702 B2 | * | 2/2004 | Rogers | G01C 3/10 356/3 |
| 7,147,371 B2 | * | 12/2006 | Hecker | A61B 6/08 378/206 |
| 7,477,927 B2 | * | 1/2009 | Stoianovici | A61B 6/032 600/424 |
| 7,545,492 B2 | * | 6/2009 | Kienitz | F41G 7/263 356/247 |
| 7,802,919 B2 | * | 9/2010 | Hessert | B23Q 17/24 378/206 |
| 8,943,701 B2 | * | 2/2015 | Hayes | G01C 15/002 33/1 G |
| 9,283,043 B2 | * | 3/2016 | Tsao | A61B 90/10 |
| 9,345,387 B2 | * | 5/2016 | Larkin | A61B 1/00087 |
| 9,398,935 B2 | * | 7/2016 | Kim | A61B 5/0062 |
| 9,655,680 B2 | * | 5/2017 | Shim | A61B 34/37 |
| 9,782,198 B2 | * | 10/2017 | Elhawary | A61B 17/34 |
| 2002/0111635 A1 | | 8/2002 | Jensen | |
| 2005/0043718 A1 | * | 2/2005 | Madhani | A61B 19/2203 606/1 |
| 2009/0099520 A1 | * | 4/2009 | Millman | A61M 1/0058 604/131 |
| 2013/0123798 A1 | | 5/2013 | Tsao | |
| 2014/0194699 A1 | * | 7/2014 | Roh | A61B 19/2203 600/249 |
| 2015/0164657 A1 | * | 6/2015 | Miles | A61F 2/4609 606/91 |
| 2015/0338728 A1 | * | 11/2015 | Amron | G03B 21/2053 33/228 |
| 2016/0354166 A1 | * | 12/2016 | Popovic | A61B 34/30 |

* cited by examiner

REMOTE CENTER OF MOTION DEFINITION USING LIGHT SOURCES FOR ROBOT SYSTEMS

CROSS-REFERENCE TO PRIOR APPLICATIONS

This application is the U.S. National Phase application under 35 U.S.C. § 371 of International Application No. PCT/IB2015/050483, filed on Jan. 22, 2015, which claims the benefit of U.S. Provisional Patent Application No. 61/935,657, filed on Feb. 4, 2014. These applications are hereby incorporated by reference herein.

BACKGROUND

Technical Field

This disclosure relates to medical instruments and more particularly to robot systems with improved remote center of motion determination.

Description of the Related Art

In robot-guided minimally invasive surgery, one or more tools are held by robotic manipulators. To ensure that the robot does not exert translational forces on incision points in a patient, some robots implement what is known as a remote center of motion (RCM) at a fulcrum point. The RCM enforces that only rotation can be performed at the port and all translational forces at that location are eliminated. In such a case, it is necessary for the RCM of the robot to be aligned with the incision point of the patient. There must therefore be a method of indication on the robot of where the RCM is located in space. Operation room personnel need to align that point in space with the incision point. Most systems need external hardware placed on the robot to be put in contact with the incision point, which increases cost and setup time. This reflects the fact that hardware indicating the location of the RCM is usually added after the robot is designed and built, and is rarely ever included as part of the robot design process.

SUMMARY

In accordance with the present principles, a robot system includes a robot linkage having arms connected by at least two joints, each joint including a joint axis of rotation and a light source aligned with the respective joint axis. The light sources are configured to direct light along the respective joint axis such that light from the light sources intersects at a position along an instrument being held in an operational position by the robot linkage to define a remote center of motion (RCM) for the robot linkage.

Another robot system includes a first joint having a first axis of rotation between at least two robot components and a second joint having a second axis or rotation between at least two robot components. An instrument is held in an operational position by the robot system. A first light source is configured to direct light along the first axis, and a second light source is configured to direct light along the second axis such that light from the first light source and the second light source intersect at a position along the instrument to define a remote center of motion (RCM) for the robot system.

A method for determining a remote center of motion includes aligning a first light source along a first axis of rotation of a joint between at least two robot components; aligning a second light source along a second axis of rotation of a joint between at least two robot components; securing an instrument in an operational position by the robot system; directing light along the first axis from the first light source; directing light along the second axis from the second light source; and defining a remote center of motion (RCM) for the robot system at an intersection of light from the first light source and the second light source at a position along the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
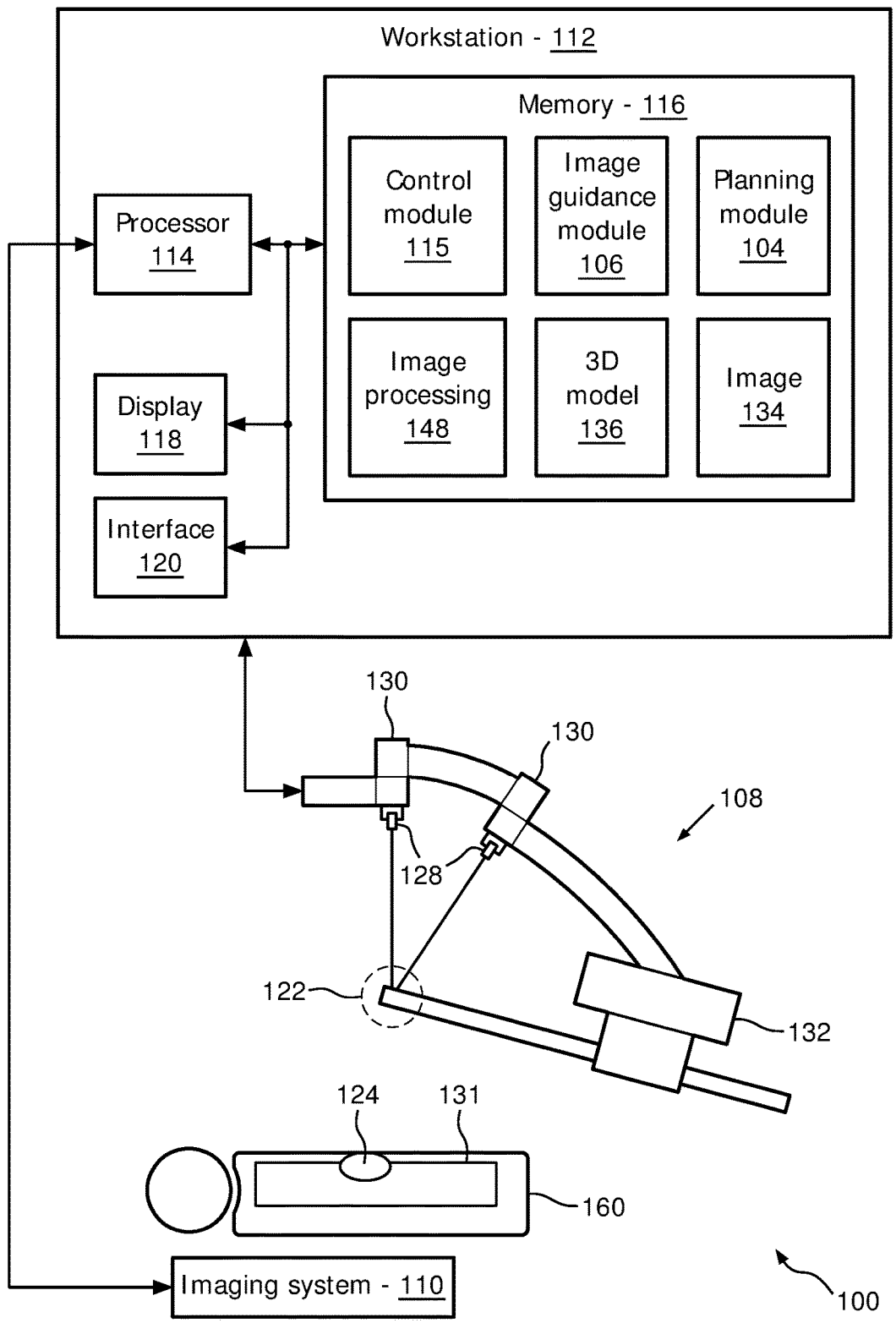
FIG. 1 is a block/flow diagram showing a robotic control workstation which employs light source definition of a remote center of motion (RCM) in accordance with one embodiment.

In accordance with the present principles, systems and methods for determining a remote center of motion (RCM) are provided to determine a robot axis that permits the use of low cost light sources to indicate a location of the RCM of a robotic system. In one embodiment, minimally invasive surgery is performed using elongated instruments (e.g., an endoscope) inserted into a patient's body through small ports. One or more of the instruments is held and controlled by a robotic device where the instruments can rotate around a fulcrum point(s), but they cannot impose translational forces on ports or the patient to prevent injury or harm to the patient. This is especially important for robotic guided surgery, as the robot can potentially exert large forces. The RCM needs to be known at a specific location in space. The point in space is then aligned with the port.

In accordance with the present principles, lasers or other lights sources are employed to indicate a location of an RCM on a robot system through an intersection of axes (i.e., light beams) at the RCM. Robot designs are disclosed to provide a robot axis which allows the use of the light system to define the RCM. If the robot is designed with an RCM, then the RCM of the robot needs to be aligned with the incision point of the patient. Methods are provided for indicating on the robot where the RCM is located in space. Once the RCM is defined, aligning the RCM in space with the incision point will be considerable less complicated for operating room personnel.

It should be understood that the present invention will be described in terms of robot systems for use with medical instruments, however, the teachings of the present invention are much broader and are applicable to any robot instruments. In some embodiments, the present principles are employed in tracking, manipulating or analyzing complex biological or mechanical systems. In particular, the present principles are applicable to procedures involving biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1, a system 100 for performing a surgical procedure using a robot is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a robot control module 115 configured to interpret commands from a user or from a program and control movement (e.g., translation and rotation), velocity, angular velocity, acceleration, angular acceleration, etc. for a robot system 108. Motion of the robot system 108 is provided using motion devices or joints 130, which may include motors, actuators, servos, etc. The robot control module 115 may include hardware (control boards, software and/or combinations thereof).

In one embodiment, workstation 112 may include a planning module 104 for storing and executing a surgical plan. The planning module 104 may provide instruction to the robot system 108 during the procedure. In another embodiment, the robot system 108 may be controlled using image guidance. An image guidance module 106 provides commands to the control systems in accordance with image data 134 collected by an instrument 102, an additional imaging system 110 (e.g., X-ray. ultrasound, etc.) and/or in accordance with image models 136 generated by scanned images (e.g., pre-operative or intra-operative image data). An image processing module 148 may be provided to convert image data into instructions for the robot system 108. It should be understood that other configurations and control systems for controlling the robot system 108 are also contemplated.

Workstation 112 may include a display 118 for viewing an internal volume 131 of a subject (patient) 160. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In a particularly useful embodiment, the robot system 108 is employed for minimally invasive surgery, although the robot system 108 may be employed in other surgical procedures and non-surgical tasks. For illustrative purposes, the robot system 108 may be employed to hold an instrument 102, such as, e.g., an endoscope with a camera or other device or instrument. Other instruments may also be employed for use during the surgery. The instrument 102 may include a catheter, a guidewire, a probe, an endoscope, a robot, an electrode, a filter device, a balloon device, forceps, clamps, other components or tools, etc. In a particularly useful embodiment, the instrument 102 passes through a remote center of motion (RCM) 122. Since many robotically manipulated instruments are rigid or semi-rigid, the instruments need to pass through the RCM 122. The RCM 122 is therefore a point on the instrument 102 and needs to be located.

In accordance with the present principles, the robot system 108 needs to be aligned with an incision point or port 124. One or more motion devices 130, e.g., joints, motor joints, pivot points etc. include a light source 128, such as a laser, light emitting diode or other focused light source. The light source 128 will be described hereinafter a laser 128. The laser 128 is directed toward a position for the RCM 122, such that when the instrument 102 is loaded in a manipulator arm 132, light from the laser 128 illuminates a position on the instrument 102 indicating the RCM 122. In one embodiment, the robot system (robot) 108 can be setup to have lasers 128 on two or more joints 130 such that the RCM 122 is defined by the intersection of lights from two or more lasers 128.

In one embodiment, the laser(s) 128 is/are mounted on the joints 130 on a side adjacent to the instrument 102. The lasers 128 are activated to indicate a position in the tool where the RCM 122 is located. The lasers 128 may include a same color, different colors and/or produce different shapes (orthogonally positioned ovals or slits), so that it will be easy to find the intersection point where beams of the lasers 128 intersect to define the RCM 122. Once the RCM 122 is defined in space and is visible on the instrument 102. The different colors may combine at the intersection point to produce a new color thereon. The user, surgeon, physician assistant, etc. can align the RCM 122 with the incision point or port 124. The lasers 128 are preferably low cost lasers that can be aligned with and applied to motor joints 130 of the robot system 108. The robot system 108 may include an arch-type architecture, although other robot architectures are also contemplated.

Figure 2:
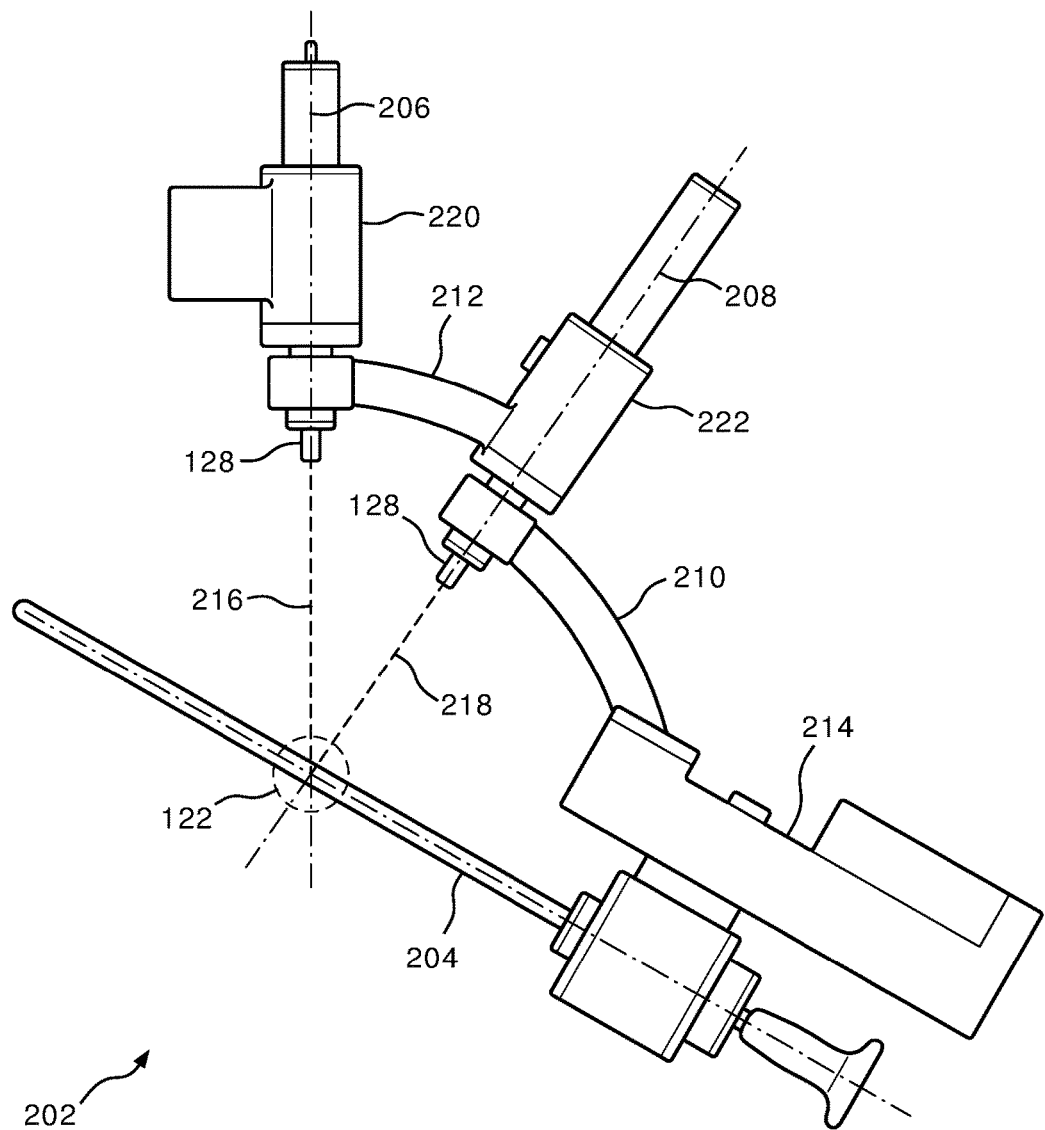
FIG. 2 is a side view of a portion of a robotic system showing a linkage with joints having lasers aligned therewith and showing an intersection of light on an instrument to define an RCM in accordance with the present principles.

Referring to FIG. 2, a robotic device or linkage 202 configured to manipulate an instrument 204 (e.g., an endoscope or other instrument) around an RCM 122 using a manipulator 214 is illustratively shown. The robot device 202 (with manipulator 214) having RCM 122 includes two serial concentric arches 210, 212. Lasers 128 are mounted on each of two joint axes 206, 208 of the robotic device 202 to intersect at the RCM 122 to indicate its location. The RCM 122 is the location in which an axis of the instrument 204, the joint axis 206 of joint 220 and the joint axis 208 of joint 222 intersect. By mounting the lasers 128 on each of the joint axes 206, 208, the location of the robot's RCM 122 can be indicated on the instrument 204 by the intersection of two laser beams 216, 218.

Once the RCM 122 is located, it is trivial for the operating room staff to align that point to the incision point on the patient. The lasers 128 indicate the RCM 122 by designing an axis assembly of the robotic device 202 in a way that allows the laser(s) 128 to be aligned to a motion axis. While robotic device 202 includes a configuration with two serial concentric arches 210, 212, for the laser 128 to be mounted on the joint axes 206, 208, the axis needs to be designed in a way that keeps motors, gearboxes, bearings and shafts aligned along a common axis (see FIG. 3). In this way, the laser 128 can be mounted at a bottom of the axis and aligned to the axis with great ease, enabling its function as a localizer of the RCM 122.

Figure 3:
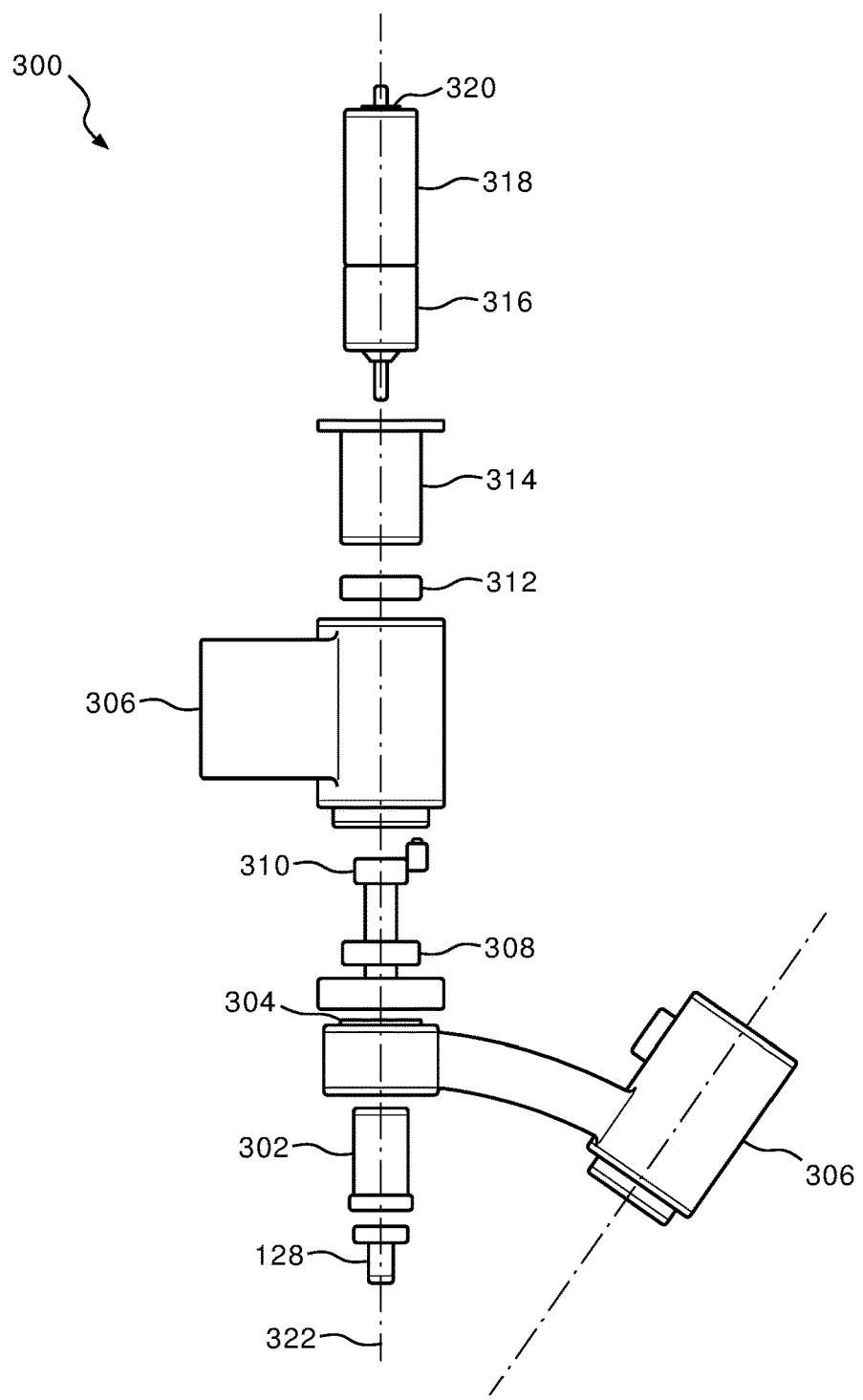
FIG. 3 is an exploded view of a joint assembly showing a laser aligned with joint components in accordance with the present principles.

Referring to FIG. 3, an exploded view of components of a joint assembly 300 is shown in-line along an axis 322 in accordance with one embodiment. The joint assembly or joint 300 includes a motor 318, an upper shaft 310 and a lower shaft 302 and bearings 308 and 312 kept aligned so that the laser 128 (and its housing) can be placed at a bottom of the joint 300 and aligned with the axis 322. The joint 300 may include an encoder 320 and an absolute encoder 304. One or more robot arms or arches 306 may be connected to the lower and upper shafts 302, 310, respectively. The motor 318 may interface with a gear box 316, which fits inside a motor housing 314 or the like. The motor 318 and gear box 316 are configured to drive the robot arms 306 relative to one another.

It should be understood that the joint 300 and its components may be configured in a different order than depicted in FIG. 3, may include other components instead of or in addition to those described and may include different shapes and structural features. In alternative embodiments, elements other than lasers may also be employed to indicate the location of the RCM 122. For example, any other optical light element, such as a light emitting diode (LED) assembly or any other type of light source, with or without other optics (e.g., lenses, etc.) may be employed. The optical light source should provide a beam that can be employed to reliably and accurately identify a position in space for the RCM 122.

It should also be understood that the present principles may be employed in a plurality of different applications including minimally invasive surgery, other robotic surgeries, robotic applications such as in manufacturing or processing; etc. Applications where the present principles are particularly useful include cardiac surgery, such as minimally invasive coronary artery bypass grafting, atrial septal defect closure, valve repair/replacement, etc.; laparoscopic surgery, such as hysterectomy, prostactomy, gall bladder surgery, etc.; or other surgeries. The other surgeries may include, e.g., natural orifice transluminal surgery (NOTES), single incision laparoscopic surgery (SILS), pulmonary/bronchoscopic surgery, minimally invasive diagnostic interventions, such as, arthroscopy, etc.

Figure 4:
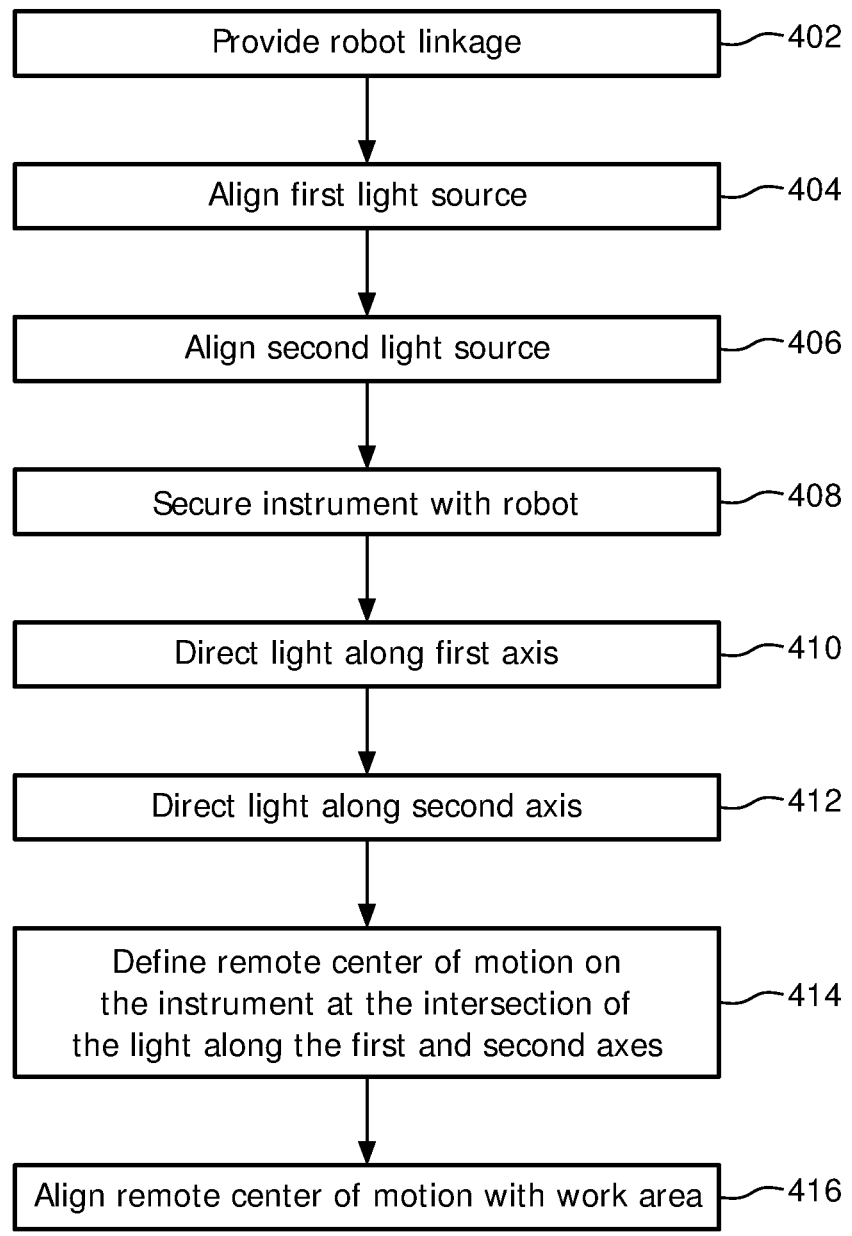
FIG. 4 is a flow diagram showing a method for defining an RCM in accordance with illustrative embodiments.

Referring to FIG. 4, a method for determining a remote center of motion is illustratively shown in accordance with the present principles. In block 402, a robot linkage is provided. The linkage may include one or more robot components, which may include passive arms, manipulator arms or other linkage members or structures. The portions of the linkage are joined by joint assemblies, which may include motors. In block 404, a first light source is aligned along a first axis of rotation of a joint between at least two robot components. In block 406, a second light source is aligned along a second axis of rotation of a joint between at least two robot components. The first light source and/or the second light source may also be aligned along respective axes with a motor, one or more shafts, a gearbox, etc. The first light source may include a different colored light or a different shaped light beam than from the second light source. The light sources may include a laser, a directed or focused incandescent light, a light emitting diode, etc.

In block 408, an instrument is secured by the robot in an operational position. The instrument may include a medical device, such as an endoscope, although other devices, medical or non-medical, may also be employed. In block 410, light is directed along the first axis from the first light source. In block 412, light is directed along the second axis from the second light source. In block 414, a remote center of motion (RCM) is defined for the robot system at an intersection of light from the first light source and the second light source at a position along the instrument. In block 416, the RCM is aligned with a work area of the robot system, e.g., in preparation for surgery or other application.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for remote center of motion definition using light sources for robot systems (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A robot system, comprising:
   a robotic device comprising one or more arms connected by at least two joints, each of the joints comprising a joint axis of rotation, and a light source aligned with the respective joint axis; each of the light sources being configured to direct light along the respective joint axis such that light from the light sources intersects at a position along an instrument being held in an operational position by the robotic device to define a remote center of motion (RCM) for the robotic device.

2. The robot system as recited in claim 1, wherein the at least two joints include at least one of a motor or at least one shaft aligned along the joint axis.

3. The robot system as recited in claim 1, wherein the light sources include one of a laser or a light emitting diode.

4. The robot system as recited in claim 1, wherein the light sources include different colors for each joint.

5. The robot system as recited in claim 1, wherein the light sources produce different beam shapes for each joint.

6. The robot system as recited in claim 1, wherein the light sources illuminate a position on the instrument to enable RCM alignment with a work area of the robot system.

7. The robot system as recited in claim 1, wherein the instrument includes a surgical tool.

8. A robot system, comprising:
   a first joint having a first axis of rotation between at least two robot components;
   a second joint having a second axis of rotation between at least two robot components;
   an instrument being held in an operational position by the robot system;
   a first light source configured to direct light along the first axis; and
   a second light source configured to direct light along the second axis such that light from the first light source and the second light source intersect at a position along the instrument to define a remote center of motion (RCM) for the robot system.

9. The robot system as recited in claim 8, wherein the first joint includes at least one of a motor or at least one shaft aligned along the first axis.

10. The robot system as recited in claim 8, wherein the second joint includes at least one of a motor or at least one shaft aligned along the second axis.

11. The robot system as recited in claim 8, wherein the first light source includes one of a laser or a light emitting diode.

12. The robot system as recited in claim 8, wherein the second light source includes one of a laser or a light emitting diode.

13. The robot system as recited in claim 8, wherein the first light source includes a different colored light than from the second light source.

14. The robot system as recited in claim 8, wherein the first light source produces a different shaped light beam than from the second light source.

15. The robot system as recited in claim 8, wherein the first light source and the second light source illuminate a position on the instrument to enable RCM alignment with a work area of the robot system.

16. A method for determining a remote center of motion, the method comprising:
   aligning a first light source along a first axis of rotation of a first joint between at least two robot components;
   aligning a second light source along a second axis of rotation of a second joint between at least two robot components;
   securing an instrument in an operational position by a robot system;
   directing light along the first axis from the first light source;
   directing light along the second axis from the second light source; and
   defining a remote center of motion (RCM) for the robot system at an intersection of light from the first light source and the second light source at a position along the instrument.

17. The method as recited in claim 16, wherein aligning the first light source includes aligning the first joint with at least one of a motor or at least one shaft along the first axis.

18. The method as recited in claim 16, wherein aligning the second light source includes aligning the second joint with at least one of a motor or at least one shaft along the second axis.

19. The method as recited in claim 16, wherein the first light source includes one of a different colored light or a different shaped light beam than from the second light source.

20. The method as recited in claim 16, wherein at least one of the first light source and/or the second light source includes one of a laser or a light emitting diode.

21. The method as recited in claim 16, further comprising aligning the RCM with a work area of the robot system.

* * * * *